US005655521A

United States Patent [19]
Faithfull et al.

[11] Patent Number: 5,655,521
[45] Date of Patent: *Aug. 12, 1997

[54] PARTIAL LIQUID BREATHING OF FLUOROCARBONS

[75] Inventors: Nicholas Simon Faithfull, Normanton by Bottesford, England; Jeffry Greg Weers, San Diego, Calif.

[73] Assignee: Alliance Pharmaceutical Corp., San Diego, Calif.

[*] Notice: The term of this patent shall not extend beyond the expiration date of Pat. No. 5,490,498.

[21] Appl. No.: 600,407

[22] Filed: Feb. 12, 1996

Related U.S. Application Data

[63] Continuation of Ser. No. 299,844, Sep. 1, 1994, Pat. No. 5,490,498, which is a continuation of Ser. No. 695,547, May 3, 1991, abandoned.

[51] Int. Cl.⁶ .................................................. A61M 15/00
[52] U.S. Cl. ...................................... 128/203.12; 128/913
[58] Field of Search ................................ 128/203.12, 913

[56] References Cited

U.S. PATENT DOCUMENTS

| | | | |
|---|---|---|---|
| 3,975,512 | 8/1976 | Long | 424/5 |
| 5,024,995 | 6/1991 | Robertson et al. | 514/21 |
| 5,158,536 | 10/1992 | Sekins et al. | 604/20 |
| 5,437,272 | 8/1995 | Fuhrman | 128/203.12 |
| 5,490,498 | 2/1996 | Faithfull et al. | 128/203.12 |

FOREIGN PATENT DOCUMENTS

| | | |
|---|---|---|
| 2245299 | 4/1973 | Germany . |
| 858824 | 8/1981 | U.S.S.R. . |
| 1143420 | 3/1985 | U.S.S.R. . |
| WO91/03267 | 3/1991 | WIPO . |

OTHER PUBLICATIONS

Pediatric Research, vol. 18, #1, 1984, "Liquid Ventilation: Effects on Pulmonary Function in Distressed Medium—Stained Lambs", by Shaffer et al., pp. 47–52.
Anesthesiology, vol. 38, #2, Feb. 1973, "Pulmonary Larage with Liquid Fluorocarbon in a Model of Pulmonary Edema", by Calderwood et al., pp. 141–144.
Curtis, et al., J. Appl. Physiol. 68(6):2322–2328. 1990.
Curtis, et al., Crit. Care Med. 19:225–230, 1991.
Derwent–Information Service, file WPIL, accession No. 91–354366 {49}, Derwent Publications Ltd., London, GB, & CA, A2035492 (Sekins) 20 Sep. 1991, see the entire abstract.
Greenspan, et al., "Liquid Ventilation of Preterm Baby", Lancet, Nov. 4, 1989, p. 1095.
Merritt, et al., Drugs 38(4):591–611, 1989.
Nakayama, et al., Crit. Care Med 19:926–933, 1991.
Ravenscraft, et al., Crit. Care Med 19:916–925, 1991.
Riess, J.G., Artificial Organs 8:44–56, 1984.
Richman, et al. Abstract 1990, World Conference on Lung Health, Boston MA.
Richman, et al., "Lung Lavage With Oxygenated Fluorocarbon Improves Gas Exchange and Lung Compliance in Cats With Acute Lung Injury", 1990 World Conference on Lung Health, Category 26.
Rufer, et al. Chest 66(Suppl.) 29S–30S (1974).
Shaffer, et al., J. Appl. Physiol. 36:208–213, 1974.
Shaffer, et al., Pediat. Res. 10:227–231, 1976.

(List continued on next page.)

*Primary Examiner*—Aaron J. Lewis
*Attorney, Agent, or Firm*—Knobbe, Martens, Olson & Bear

[57] ABSTRACT

The present invention includes a method for treating a patient in need of facilitated oxygen delivery through the lungs, additional lung surfactant, removal of material from inside the lung, or inflation of collapsed portions of the lung, comprising the step of introducing into the lung of the patient an effective therapeutic amount of a fluorocarbon liquid, the amount not exceeding the functional residual capacity of the lung of the patient upon exhalation taking into account any positive and expiratory pressure applied to the patient's lung. The method may also comprise the additional step of providing an oxygen-containing breathing gas to the patient while the fluorocarbon liquid is in the lung.

44 Claims, 3 Drawing Sheets

OTHER PUBLICATIONS

Shaffer, et al., Chest. Res. 17:303–306, 1983.

Shaffer, et al., "Physiological Effects of Ventilation With Liquid Fluorocarbon at Controlled Temperatures", Undersea Biomedical Research, vol. 11, No. 3, 1984.

Waldrop, "The (Liquid) Breath of Life", Science, 245:1043–1045.

Widjaja, et al., "Mechanical Properties of Isolated Fetal Miniature Pig Lungs After Substitution . . . ", Res. Exp Med., 188:425–432 (1988).

Yokoyama, et al., Artif. Organs 8:34–40, 1984.

PARTIAL LIQUID BREATHING OF FLUOROCARBONS

This application is a continuation of application U.S. Ser. No. 08/299,844, filed Sep. 1, 1994, now U.S. Pat. No. 5,490,498 which is a continuation of U.S. Ser. No. 07/695,547, filed May 3, 1991, now abandoned.

FIELD OF THE INVENTION

The present invention relates generally to lung surfactant supplements and methods for treating pulmonary diseases. The invention specifically discloses partial liquid breathing techniques and the use of biocompatible liquid fluorocarbons in treatment of various pulmonary conditions.

BACKGROUND OF THE INVENTION

Lung surfactant is composed of a complex mixture of phospholipid, neutral lipid and protein. Surfactant is roughly 90% lipid and 10% protein with a lipid composition of 55% diphosphotidylcholine (DPPC), 25% phosphatidylcholine (PC), 12% phosphatidylglycerol (PG), 3.5% Phosphatidlyethanolamine (PE), sphingomyelin and phosphatidylinositol (PI).

Lung surfactant functions to reduce surface tension within the alveoli. It mediates transfer of oxygen and carbon dioxide, promotes alveolar expansion and covers the lung surfaces. Reduced surface tension permits the alveoli to be held open under less pressure. In addition, lung surfactant maintains alveolar expansion by varying surface tension with alveolar size (*The Pathologic Basis of Disease*, Robbins and Cotran eds. W. B. Saunders Co. New York, 1979). There are a number of medical therapies or regimes that would benefit from the use of surfactant supplements. For example, surfactant supplementation is beneficial for individuals with lung surfactant deficiencies. In addition, there are a variety of medical procedures requiring that fluids be added to the lung, for example, as a wash to remove endogenous or exogenous matter. The use of a biocompatible liquid for these applications would be advantageous. Routinely, balanced salt solutions or balanced salt solutions in combination with a given therapeutic agent are provided as an aspirate or as a lavage for patients with asthma, cystic fibrosis or bronchiectasis. While balanced saline is biocompatible, lavage procedures can remove endogenous lung surfactant. Further, lavage with such aqueous liquids may not permit adequate delivery of oxygen to the body. Therefore, it is contemplated that the use of substances having at least some of the functional properties of lung surfactant could decrease lung trauma and provide an improved wash fluid.

At present, surfactant supplements are used therapeutically when the amount of lung surfactant present is not sufficient to permit proper respiratory function. Surfactant supplementation is most commonly used in Respiratory Distress Syndrome (RDS), also known as hyaline membrane disease, when surfactant deficiencies compromise pulmonary function. While RDS is primarily a disease of newborn infants, an adult form of the disease, Adult Respiratory Distress Syndrome (ARDS), has many of the same characteristics as RDS, thus lending itself to similar therapies.

Adult respiratory distress occurs as a complication of shock-inducing trauma, infection, burn or direct lung damage. The pathology is observed histologically as diffuse damage to the alveolar wall, with hyaline membrane formation and capillary damage. Hyaline membrane formation, whether in ARDS or RDS, creates a barrier to gas exchange. Decreased oxygen produces a loss of lung epithelium yielding decreased surfactant production and foci of collapsed alveoli. This initiates a vicious cycle of hypoxia and lung damage.

RDS accounts for up to 5,000 infant deaths per year and affects up to 40,000 infants each year in the United States alone. While RDS can have a number of origins, the primary etiology is attributed to insufficient amounts of pulmonary surfactant. Those at greatest risk are infants born before the 36th week of gestation having premature lung development. Neonates born at less than 28 weeks of gestation have a 60–80% chance of developing RDS. The maturity of the fetal lung is assessed by the lecithin/sphingomyelin (L/S) ratio in the amniotic fluid. Clinical experience indicates that when the ratio approximates 2:1, the threat of RDS is small. In those neonates born from mothers with low L/S ratios, RDS becomes a life-threatening condition.

At birth, high inspiratory pressures are required to expand the lungs. With normal amounts of lung surfactant, the lungs retain up to 40% of the residual air volume after the first breath. With subsequent breaths, lower inspiratory pressures adequately aerate the lungs since the lungs now remain partially inflated. With low levels of surfactant, whether in infant or adult, the lungs are virtually devoid of air after each breath. The lungs collapse with each breath and the neonate must continue to work as hard for each successive breath as it did for its first. Thus, exogenous therapy is required to facilitate breathing and minimize lung damage.

Type II granular pneumocytes synthesize surfactant using one of two pathways dependent on the gestational age of the fetus. The pathway used until about the 35th week of pregnancy produces a surfactant that is more susceptible to hypoxia and acidosis than the mature pathway. A premature infant lacks sufficient mature surfactant necessary to breathe independently. Since the lungs mature rapidly at birth, therapy is often only required for three or four days. After this critical period the lung has matured sufficiently to give the neonate an excellent chance of recovery.

In adults, lung trauma can compromise surfactant production and interfere with oxygen exchange. Hemorrhage, infection, immune hypersensitivity reactions or the inhalation of irritants can injure the lung epithelium and endothelium. The loss of surfactant leads to foci of atelectasis. Tumors, mucous plugs or aneurysms can all induce atelectasis, and these patients could therefore all benefit from surfactant therapy.

In advanced cases of respiratory distress, whether in neonates or adults, the lungs are solid and airless. The alveoli are small and crumpled, but the proximal alveolar ducts and bronchi are overdistended. Hyaline membrane lines the alveolar ducts and scattered proximal alveoli. The membrane consists of protein-rich, fibrin-rich edema admixed with cellular debris.

The critical threat to life in respiratory distress is inadequate pulmonary exchange of oxygen and carbon dioxide resulting in metabolic acidosis. In infants this, together with the increased effort required to bring air into the lungs, produces a lethal combination resulting in overall mortality rates of 20–30%.

Optimally, surfactant supplements should be biologically compatible with the human lung. They should decrease the surface tension sufficiently within the alveoli, cover the lung surface easily and promote oxygen and carbon dioxide exchange.

Ventilation assistance is commonly used to provide sufficient oxygen to surfactant deficient patients. These ventilation regimes include continuous positive airway pressure, or continuous distending pressure procedures.

Recently, surfactant replacement therapy has been used either alone or in combination with ventilation therapy. Initial work with surfactant replacements used preparations of human lung surfactant obtained from lung lavage. The layaged fluid is collected and the surfactant layer naturally separates from the saline wash. This layer is harvested and purified by gradient centrifugation. These preparations worked well as surfactant replacements for RDS and thus provided some of the original data to suggest that surfactant replacement was a necessary therapy. Supplies of human surfactant are limited and expensive, and therefore alternate sources of surfactant were investigated for use in replacement therapies.

The second generation of surfactant substitutes are purified preparations of bovine and porcine lung surfactant. Preparations of bovine lung surfactant have been administered to many surfactant deficient patients. Like human surfactant, bovine lung surfactant is difficult to prepare. Sources are few and availability is limited. Further, while the use of bovine lung surfactant in neonares does not present a problem immunologically, bovine surfactant applications in adults could immunologically sensitize patients to other bovine products.

To minimize the immunologic problems associated with the use of bovine lung surfactant, the harvested surfactant is further extracted with chloroform/methanol to purify the lipid component. This work led to the discovery that there are three major proteins (SP-A, SP-B and SP-C) associated with lung surfactant. All three are postulated to have some beneficial role in surfactant function. SP-A is hydrophobic and has some documented antibacterial activity. SP-B is most closely associated with traditional surfactant function. These proteins can be purified or cloned, expressed and added back to purified lipid preparations. However, these procedures are also time consuming. In addition, the use of purified animal-derived surfactant protein creates the same immunologic problems noted above.

Some of the functional domains within each of the surfactant proteins are now mapped and the individual lipid components of lung surfactant are being tested to determine if a semi-synthetic or synthetic product can be used effectively to replace purified endogenous surfactant. To this end, synthetic peptides of SP-B have been added to mixtures of DPPC and PG to create an artificial surfactant product.

An artificial surfactant would readily cover the lung surfaces and facilitate oxygen exchange. The surfactant would be sterilizable, amenable to large scale production and be relatively stable for convenient storage and physician convenience.

Fluorocarbons are fluorine substituted hydrocarbons that have been used in medical applications as imaging agents and as blood substitutes. U.S. Pat. No. 3,975,512 to Long uses fluorocarbons, including brominated perfluorocarbons, as a contrast enhancement medium in radiological imaging. Brominated fluorocarbons and other fluorocarbons are known to be safe, biocompatible substances when appropriately used in medical applications.

It is additionally known that oxygen, and gases in general, are highly soluble in some fluorocarbons. This characteristic has permitted investigators to develop emulsified fluorocarbons as blood substitutes. For a general discussion of the objectives of fluorocarbons as blood substitutes and a review of the efforts and problems in achieving these objectives see "Reassessment of Criteria for the Selection of Perfluorochemicals for Second-Generation Blood Substitutes: Analysis of Structure/Property Relationship" by Jean G. Reiss, *Artificial Organs* 8:34–56, 1984.

Oxygenarable fluorocarbons act as a solvent for oxygen. They dissolve oxygen at higher tensions and release this oxygen as the partial pressure decreases. Carbon dioxide is handled in a similar manner. Oxygenation of the fluorocarbon when used intravascularly occurs naturally through the lungs. For other applications, such as percutaneous transluminal coronary angioplasty, stroke therapy and organ preservation, the fluorocarbon can be oxygenated prior to use.

Liquid breathing has been demonstrated on several occasions. An animal may be submerged in an oxygenated fluorocarbon liquid and the lungs may be filled with fluorocarbon. Although the work of breathing is increased in these total submersion experiments, the animal can derive adequate oxygen for survival from breathing the fluorocarbon liquid.

Liquid breathing as a therapy presents significant problems. Liquid breathing in a hospital setting requires dedicated ventilation equipment capable of handling liquids. Moreover, oxygenation of the fluorocarbon being breathed must be accomplished separately. The capital costs associated with liquid breathing are considerable.

It is an object of the present invention to provide a method for treating lung surfactant deficiency through use of fluorocarbon liquids.

A further object of the invention is to provide a method for therapeutic use of fluorocarbon liquids in the lungs that does not require liquid-handling ventilation equipment. Instead, traditional gas ventilation equipment can be used.

Still a further object of the present invention is to apply pulmonary administration of fluorocarbon liquids to a wide range of diseases and medical conditions.

These and other objects of the invention are discussed in the detailed description of the invention that follows.

SUMMARY OF THE INVENTION

The present invention includes a method for treating a patient in need of facilitated oxygen delivery through the lungs, additional lung surfactant, removal of material from inside the lung, or inflation of collapsed portions of the lung, comprising the step of introducing into the lung of the patient an effective therapeutic amount of a fluorocarbon liquid, the amount not exceeding the functional residual capacity of the lung of the patient upon exhalation taking into account any positive and expiratory pressure applied to the patient's lung. The method may also comprise the additional step of providing an oxygen-containing breathing gas to the patient while the fluorocarbon liquid is in the lung.

In addition, a patient in need of additional lung surfactant may receive the fluorocarbon liquid as a lung surfactant replacement. In a preferred embodiment the amount of fluorocarbon liquid introduced into the lungs is at least about 0.1% of the patient's total lung capacity and not more than about 50% of the patient's total lung capacity, wherein the total lung capacity comprises the fluid volume of the lung when fully inflated during normal breathing. A preferred fluorocarbon is a brominated fluorocarbon and a still more fluorocarbon is perfluorooctylbromide. It is additionally contemplated that the equilibrium coefficient of spreading of the fluorocarbon is a positive number and more preferably that the equilibrium coefficient of spreading of the fluorocarbon be at least 1.0.

The amount of fluorocarbon liquid introduced into the patient's lung is contemplated to be at least 0.1 ml/kg of the patient's body weight and not more than about 50 ml/kg patient body weight.

It is further contemplated that the respiration of the patient while the fluorocarbon is in the lung can be facilitated by external ventilation equipment. In addition, it is contemplated that fluorocarbons can be used for partial liquid ventilation in patients having a respiratory distress syndrome and further that the method is effective to alleviate the respiratory distress syndrome. Another preferred use of fluorocarbon in the lung comprises the use of fluorocarbons for patients in need of removal of material from inside the lung, comprising the step of removing the fluorocarbon liquid, together with the material, from the lung. An additional method for the removal of material from the lung, comprises the steps of permitting the material to float on the fluorocarbon, and removing the floating material from the lung.

Fluorocarbon liquid can additionally be administered in combination with a hydrophilic pharmacologic agent in particulate form. It is further contemplated that the pharmacologic agent is a hydrophilic lung surfactant in powdered form. In addition, fluorocarbon is provided to patients in need of facilitated oxygen delivery through the lungs and for those patients receiving oxygen-containing breathing gas, it is contemplated that the oxygen containing breathing gas is oxygen.

DETAILED DESCRIPTION OF THE INVENTION

Figure 1:
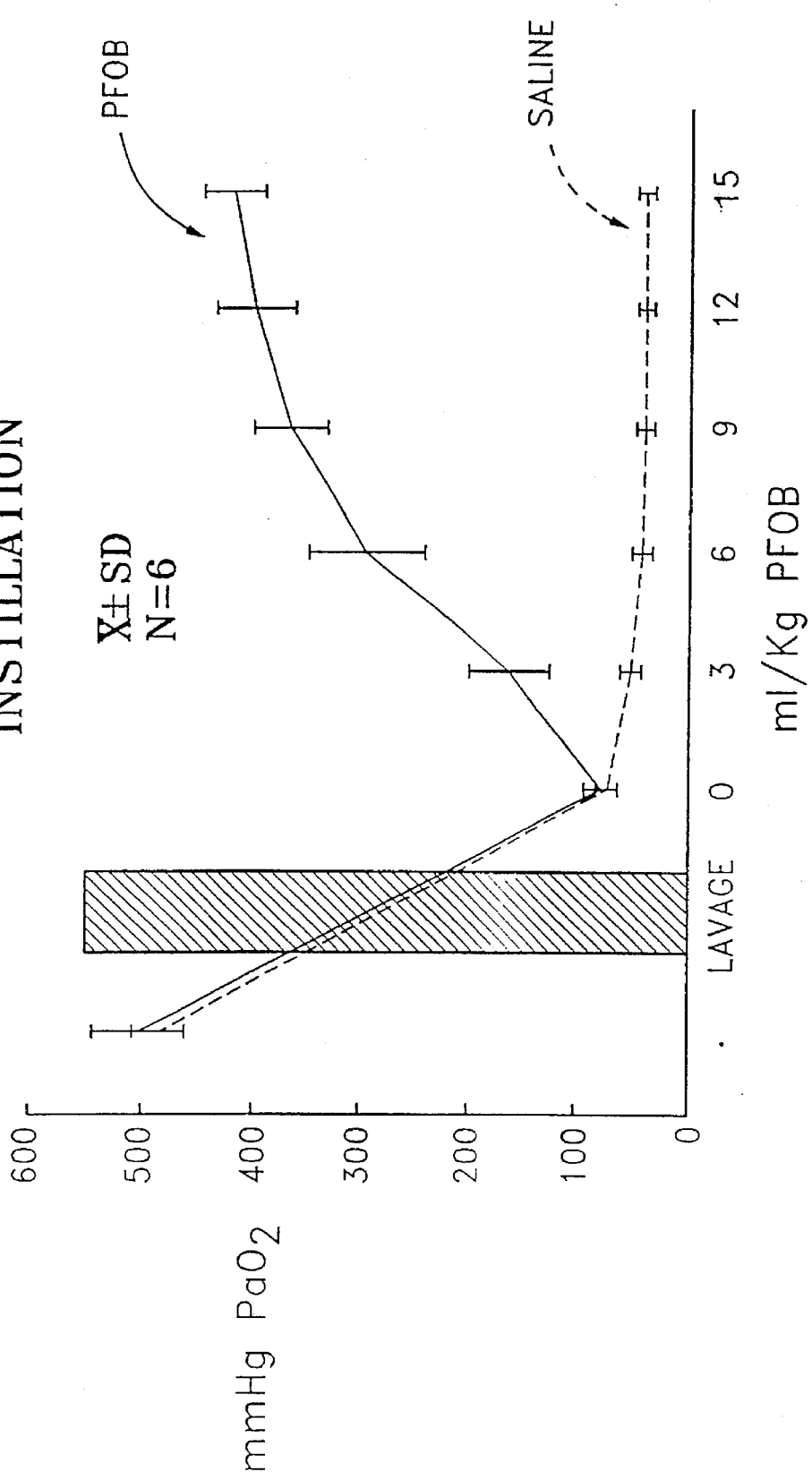
FIG. 1 is a graphic representation of the effect of intratracheal perfluorooctylbromide instillation of the blood oxygen levels in rabbits following lung lavage to remove endogenous surfactant as compared with intratracheal saline instillation.

As noted, lung surfactant supplements should be nontoxic and biologically compatible. Like human surfactant, surfactant supplements should decrease the surface tension within the alveoli and promote oxygen and carbon dioxide exchange. Additionally these substitutes should spread easily over the lung surfaces to maximize gas interchange. Such a surfactant would enhance gas exchange, thus reducing cyanosis and metabolic acidosis.

Surfactant replacements that do not spread easily within the lung will tend to concentrate in pools and be less than optimally effective. Surfactant supplements should be readily available to the physician. In addition, they should be provided as a sterile product having reasonable chemical stability and a sufficient shelf-life.

Compounds useful in this invention, such as those listed below (hereinafter called "fluorocarbons") are generally able to promote gas exchange, and most of these fluorocarbons readily dissolve oxygen and carbon dioxide. There are a number of fluorocarbons that are contemplated for medical use. These fluorocarbons include bis (F-alkyl) ethanes such as $C_4F_9CH=CH_4CF_9$ (sometimes designated "F-44E"), i-$C_3F_9CH=CHC_6F_{13}$ ("F-i36E"), and $C_6F_{13}CH=CHC_6F_{13}$ ("F-66E"); cyclic fluorocarbons, such as C10F18 ("F-decalin", "perfluorodecalin" or "FDC"), F-adamantane ("FA"), F-methyladamantane ("FMA"), F-1,3-dimethyladamantane ("FDMA"), F-di-or F-trimethylbicyclo [3.3.1]nonane ("nonane"); perfluorinated amines, such as F-tripropylamine ("FTPA") and F-tri-butylamine ("FTBA"), F-4-methyloctahydroquinolizine ("FMOQ"), F-n-methyl-decahydroisoquinoline ("FMIQ"), F-n-methyldecahydroquinoline ("FHQ"), F-n-cyclohexylpurrolidine ("FCHP") and F-2-butyltetrahydrofuran ("FC-75" or "RM101").

Other fluorocarbons include brominated perfluorocarbons, such as 1-bromo-heptadecafluoro-octane ($C_8F_{17}Br$, sometimes designated perfluorooctylbromide or "PFOB"), 1-bromopentadecafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, perfluorooctyl hydride, and similar compounds having different numbers of carbon atoms. In addition, the fluorocarbon may be neat or may be combined with other materials, such as surfactants (including fluorinated surfactants) and dispersed materials.

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO-(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}$-$C_{n'}F_{2n'+1}$, $C_nF_{2n+1}OC_{n'}F_{2n'+1}$, or $C_nF_{2n+1}CF=CHC_{n'}F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$. It will be appreciated that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated. Additional "fluorocarbons" not listed here, but having those properties described in this disclosure that would lend themselves to pulmonary therapies are additionally contemplated.

Some fluorocarbons have relatively high vapor pressures which render them less suitable for use as a surfactant replacement and for partial liquid breathing. These include 1-bromotridecafluorohexane ($C_6F_{13}Br$) and F-2-butyltetrahyddrofuran ("FC-75" or "RM101"). Lower vapor pressures are additionally important from an economic standpoint since significant percentages of fluorocarbon having high vapor pressure would be lost due to vaporization during the therapies described herein. In a preferred embodiment, fluorocarbons having lower surface tension values are chosen as surfactant supplements.

The fluorocarbon of choice should have functional characteristics that would permit its use temporarily as a lung surfactant, for oxygen delivery, in removal of material from the interior of the lung, or for inflation of collapsed portions of the lung. Fluorocarbons are biocompatible and most are amenable to sterilization techniques. For example, they can be heat-sterilized (such as by autoclaving) or sterilized by radiation. In addition, sterilization by ultrafiltration is also contemplated.

One group of preferred fluorocarbons have the ability to reduce the surface tension in the lung. As noted above, surfactants function to decrease the tension between the surface molecules of the alveolar fluid. The lung surfactant is solubilized in a water-continuous fluid lining the alveolus. Typically, the surface tension in the absence of lung surfactant is ca. 60 dynes/cm decreasing to 5–30 dynes/cm in the presence of lung surfactant. Fluorocarbons have low surface tension values (typically in the range of 20 dynes/cm) and have the added benefit of dissolving extremely large quantities of gases such as oxygen and carbon dioxide. Perfluorocarbons are particularly suited for this use, and brominated fluorocarbons are particularly preferred.

Although reduction in surface tension is an important parameter in judging fluorocarbons and perfluorocarbons as potential lung surfactant supplements or for use in partial liquid breathing, a novel and non-obvious characteristic of some fluorocarbons is their apparent ability to spread over the entire respiratory membrane. The ability of some fluorocarbons to spread evenly and effectively over lung surfaces may be of even greater importance than the ability of fluorocarbons to reduce surface tension.

The total surface area of the respiratory membrane is extremely large (ca. 160 square meters for an adult). Thus, an effective fluorocarbon for partial liquid breathing should be able to cover the lung surfaces with relatively little volume.

The ability of a given substance to cover a measured surface area can be described by its spreading coefficient. The spreading coefficients for fluorocarbons can be expressed by the following equation:

$$S(o \text{ on } w) = \gamma_{w/a} - (\gamma_{w/o} + \gamma_{o/a})$$

Where S (o on w) represents the spreading coefficient; $\gamma$=interfacial tension; w/a=water/air; w/o=water/oil; and o/a=oil/air.

If the fluorocarbon exhibits a positive spreading coefficient, then it will spread over the entire surface of the respiratory membrane spontaneously. Fluorocarbons having spreading coefficients of at least one are particularly preferred. If the spreading coefficient is negative, the compound will tend to remain as a lens on the membrane surface. Adequate coverage of the lung surface is important for restoring oxygen and carbon dioxide transfer and for lubricating the lung surfaces to minimize further pulmonary trauma.

The spreading coefficients for a number of perfluorocarbons are reported in Table 1. Each perfluorocarbon tested is provided together with its molecular weight and the specific variables that are used to calculate the spreading coefficient S (o on w). The perfluorocarbons reported are PFOB, perfluorotributylamine (FC-17), perfluorodecalin (APF-140), dimethyl perfluorodecalin (APF-175), trimethyl decalin (APF-200), perfluoroperhydrophenanthrene (APF-215 ), pentamethyl decal in (APF-240), and octamethyl decalin (APF-260).

These perfluorocarbons are representative of groups of perfluorocarbons having the same molecular weight that would produce similar spreading coefficients under similar experimental conditions. For example, it is expected that ethyl perfluorodecalin will have a spreading coefficient similar to that of dimethylperfluorodecalin. Propyl or tri 3 carbon-substituted decalin would have a spreading coefficient similar to that reported for trimethyl decalin, pentamethyldecalin is representative of other decalins substituted with 5 substituent carbons, and octamethyldecalin is also representative of other combination substituted decalins of identical molecular weight.

TABLE I

Spreading coefficients of perfluorocarbons on saline (T = 25 C)

| Perfluorocarbon | MW (g/mol) | $\gamma_{o/a}$ (mN/m) | $\gamma_{o/w}$ (mN/m) | S (o on w) |
|---|---|---|---|---|
| PFOB (perfluorooctylbromide) | 499 | 18.0 | 51.3 | +2.7 |
| FC-47 (perfluorotributylamine) | 671 | 17.9 | 55.1 | −1.0 |
| APF-140 (perfluorodecalin) | 468 | 18.2 | 55.3 | −1.5 |
| APF-175 (dimethyl decalin) | 570 | 20.7 | 55.9 | −4.6 |
| APF-200 (trimethyl decalin) | 620 | 21.4 | 55.9 | −5.3 |
| APF-215 (perfluoroperhydrophenanthrene) | 630 | 21.6 | 56.0 | −5.6 |
| APF-240 (pentamethyl decalin) | 770 | 22.6 | 56.3 | −6.9 |
| APF-260 (octamethyl decalin) | 870 | 22.4 | 56.1 | −6.5 |

It can be seen from this limited sampling of fluorocarbons that perfluorooctylbromide (PFOB) provides a positive spreading coefficient. In addition, PFOB has a low vapor pressure (14 tort @ 37° C.), further illustrating that PFOB is a particularly preferred choice for use as a lung surfactant replacement. Because of the reduced vapor pressure, PFOB will have a decreased tendency to vaporize during use. Perfluorodecalin (APF-140) and perfluoroamine (FC-47) have also been tested in potential blood substitute formulations. These compounds exhibit negative spreading coefficients on saline. However, other perfluorocarbons, similar to APF-140 and FC-47, but having decreasing molecular weights, exhibited decreasing surface tensions and increasing spreading coefficients. This suggests that lower molecular weight perfluorocarbons might also have useful spreading coefficients. However, decreasing molecular weight will increase vapor tension and make the compounds less suitable for this use.

The following examples provide information relating to the effect of PFOB treatment on respiratory insufficiency in an experimental rabbit model. The general protocol for partial liquid ventilation of the rabbits is described below.

Animal Preparation

New Zealand rabbits weighing between 2.8 and 3.0 kg were anesthetized with 50 mg/kg of phenobarbital sodium iv and a cannula was inserted through a tracheotomy midway along the trachea with its tip proximal to the carina. Ventilation with a Servo ventilator 900C (Siemens-Elema, Sweden) was initiated using pure oxygen and zero end-expiratory pressure with a constant tidal volume of 12 ml/kg, frequency of 30/min and inspiratory time of 35%. Anesthesia was maintained with additional doses of pentobarbital, as required, and pancuronium bromide was administered as an intravenous bolus (0.1 mg/kg) and followed by a continuous infusion (0.1 mg/kg/hr) for muscle paralyzation. A solution of 5% dextrose and 0.45% NaCl was administered continuously at a rate of 10 ml/kg/hr as a maintenance fluid. A heating pad maintained core temperature at 37°±1° C., monitored by an esophageal thermistor (Elektroalboratoriet, Copenhagen).

Left femoral artery and vein were each cannulated with polyvinyl catheters for arterial and central venous pressure recording and blood sampling. A special indwelling catheter (Mikro-pO$_2$-Messkatheter, Licox) was inserted into the right femoral artery for continuous oxygen pressure monitoring (Licox, GMS, Germany). Arterial blood gas and Hb (hemoglobin) measurements were made by Osm-2 Hemoximeter and ABL-330 (Radiometer Copenhagen). Lung mechanics and endtidal $CO_2$ were measured by means of Lung Mechanics Calculator 940 (Siemens-Elema, Sweden) and $CO_2$ Analyzer 930 (Siemens-Elema, Sweden), respectively. Intravascular pressure monitoring was made by using a Statham P23XL transducer (Spectramed, USA) and all tracings including ECG were recorded by a Sirecust 1280 recorder (Siemens).

Model of Respiratory Insufficiency

After the control observations were made, lung lavage with 30ml/kg of warm saline (37° C.) was performed to induce respiratory insufficiency. After the first lavage, positive end expiratory pressure (PEEP) was increased to 6 $cmH_2O$ and lung layages were repeated to get an arterial $pO_2$ below 100 mmHg with the initial ventilatory settings (between 4–6 layages). The same ventilation mode was used throughout the experiment (volume control ventilation; $F_iO_2$:1, tidal volume: 12 ml/kg, PEEP: 6 cm $H_2O$, frequency: 30/min, inspiratory time: 35%).

Partial Liquid Ventilation Procedure

After respiratory insufficiency was induced, PFOB liquid was administered through the tracheal cannula into the animal's lungs with incremental doses of 3 ml/kg up to a total volume of 15 ml/kg. Animals were ventilated for 15 minutes after each dose of PFOB instillation with the same ventillatory settings as mentioned above and thereafter arterial blood gases, cardiocirculatory parameters and pulmonary mechanics were measured. After the last dose PFOB measurements, animals were sacrificed by administration of high dose pentobarbital.

EXAMPLE 1

Mean Arterial Oxygen Tensions Following PFOB Administration

FIG. 1 is a graphic representation of the results of the experimental protocol described above. The mean arterial oxygen tension in the six rabbits tested was 504.2 mmHg. Following lung lavage to remove surfactant the arterial oxygen tension dropped to a mean value of 75.1 mmHg. The administration of increasing volumes of PFOB resulted in increasing arterial oxygen tensions. Doses of 15 ml/kg of PFOB increased oxygen pressures to 83% of their original value. These results are compared to the use of saline for partial liquid ventilation. Increasing volumes of saline in place of PFOB yielded an additional drop in arterial oxygen pressure. This data indicates that the administration of the perfluorocarbon PFOB significantly improved the arterial oxygen tension in the experimental animals as compared to saline treated controls.

EXAMPLE 2

Mean Arterial Carbon Dioxide Tensions Following PFOB Administration

Figure 2:
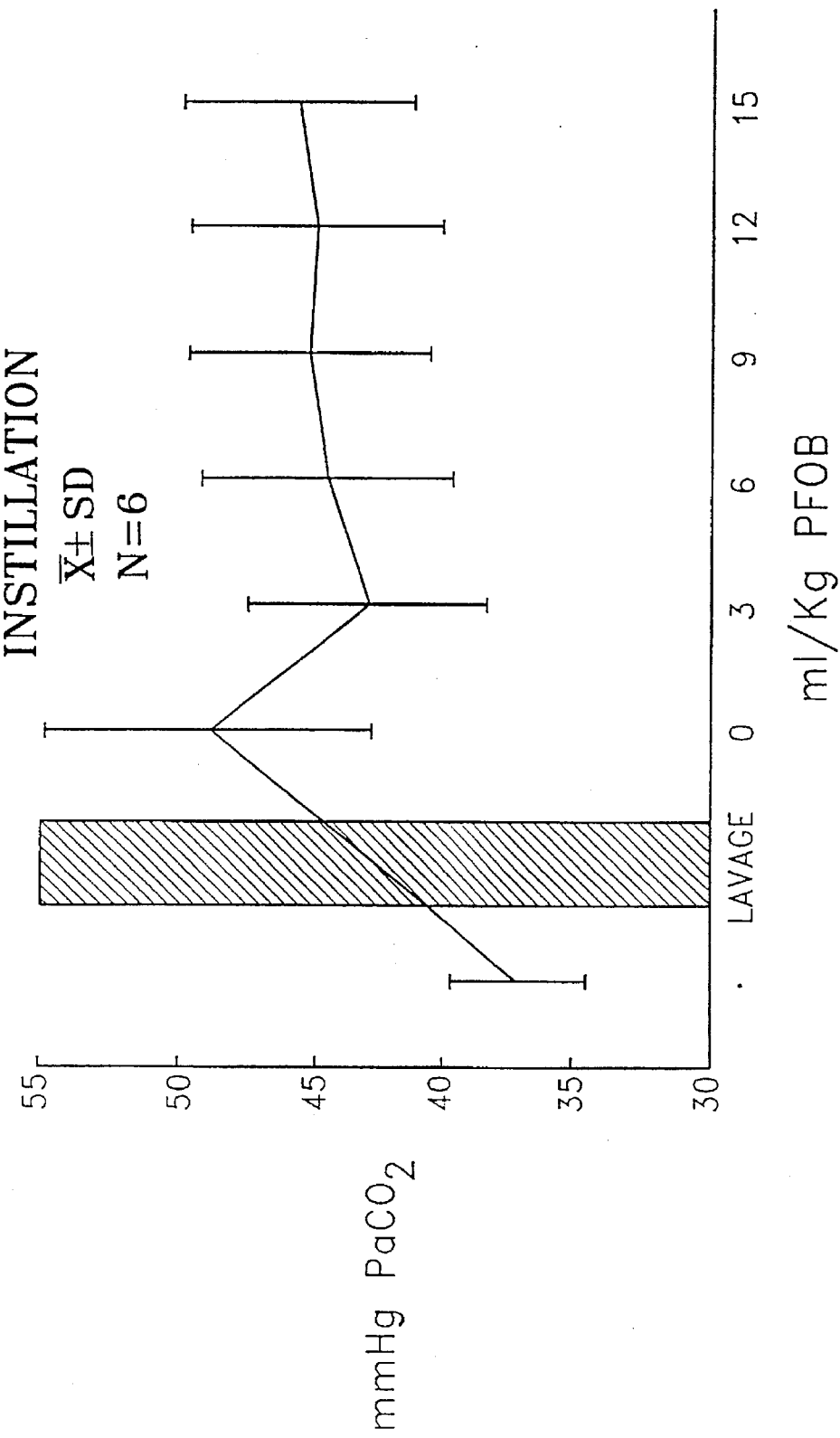
FIG. 2 is a graphic representation of the effect of intratracheal perfluorooctylbromide instillation on blood carbon dioxide levels in rabbits following lung lavage to remove endogenous surfactant.

Mean arterial carbon dioxide tensions were calculated following lung lavage using the experimental protocol described above. FIG. 2 is a graphic representation of these results. Before lavage the average arterial carbon dioxide tensions in the lungs was 37 mmHg. Following the lavage procedure the carbon dioxide levels increased to 48.7 mmHg. This level decreased after administration of PFOB, indicating that $CO_2$ transport was also facilitated by PFOB administration.

EXAMPLE 3

Mean Airway Pressures Following PFOB Administration

Figure 3:
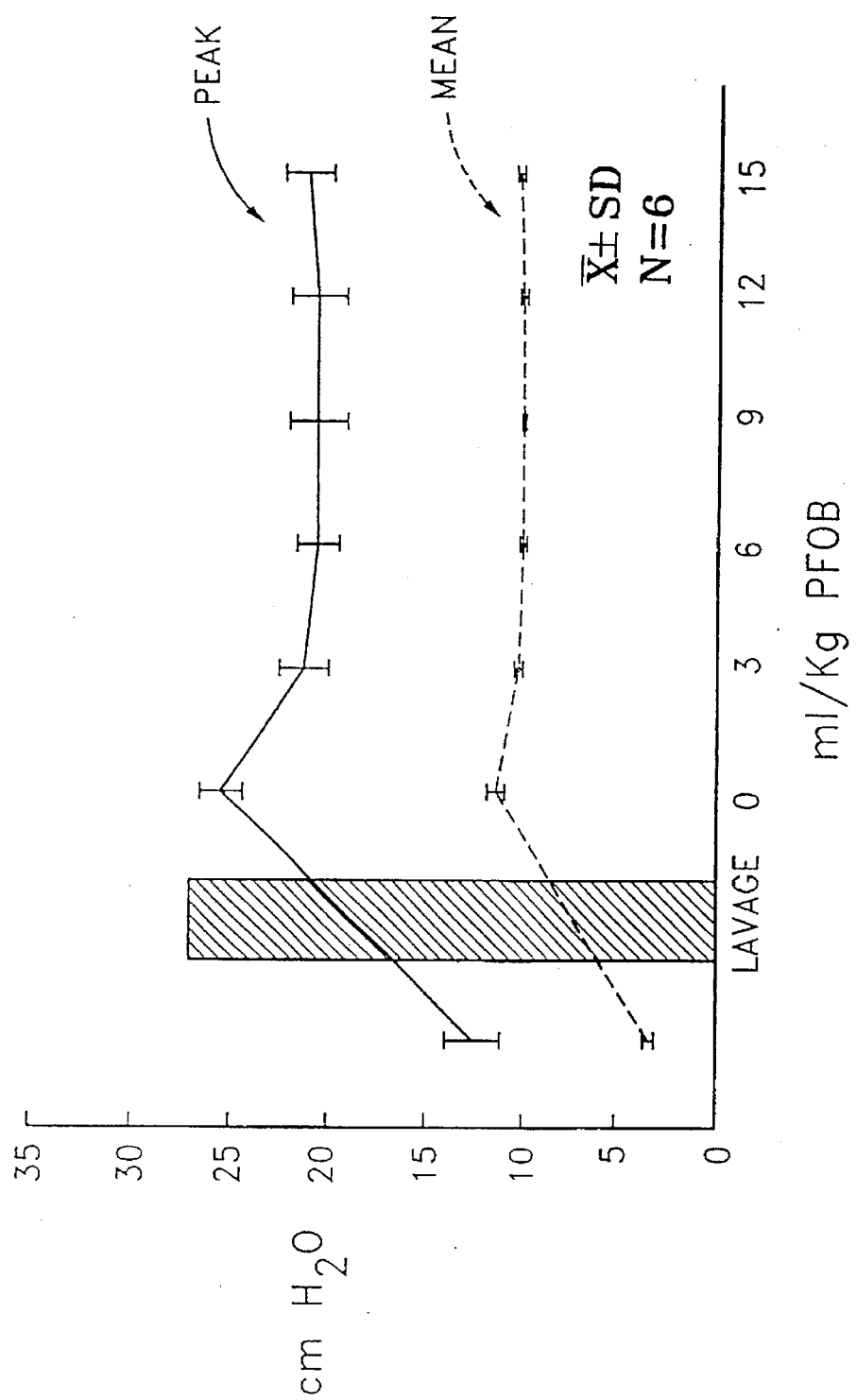
FIG. 3 is a graphic representation of the effect of intratracheal perfluorooctlybromide instillation on mean and peak lung airway pressures in rabbits following lung lavage to remove endogenous surfactant.

Mean airway pressures were determined following PFOB supplementation of surfactant deficient animals. FIG. 3 shows mean airway pressures measured in $cmH_2O$ as a function of increasing volumes of PFOB added. Following lung lavage the airway pressures increased due to surfactant depletion. PFOB supplementation decreased mean airway pressure.

The data for Examples 1–3 are provided in Table 2.

| | BEFORE LAVAGE | ARDS | INTRATRACHEAL PFOB ml/kg | | | | |
|---|---|---|---|---|---|---|---|
| | | | 3 | 6 | 9 | 12 | 15 |
| $P_aO_2$ mmHg | | | | | | | |
| X | 504.2 | 75.1 | 159.6 | 296.7 | 365.7 | 398.2 | 419.9 |
| SD | 39.7 | 15.0 | 38.1 | 54.4 | 33.4 | 35.7 | 27.3 |
| $P_aCO_2$ mmHg | | | | | | | |
| X | 37.0 | 48.7 | 42.8 | 44.4 | 45.0 | 44.8 | 45.5 |
| SD | 2.6 | 6.0 | 4.7 | 4.8 | 4.6 | 4.8 | 4.4 |
| Peak Airway Pressure $cmH_2O$ | | | | | | | |
| X | 12.4 | 25.5 | 21.3 | 20.6 | 20.6 | 20.6 | 21.1 |
| SD | 1.4 | 1.0 | 1.4 | 1.2 | 1.6 | 1.5 | 1.4 |

Both fetal and adult rabbits have been used to study Respiratory Distress Syndrome. Much of the work with surfactant replacements was initiated in these animals. For studies on RDS therapies, the method of fetal animal ventilation used should closely mimic the ventilation methods used for the neonate. Other fetal and adult animals studied include lamb, dog or baboon. In vivo studies in animals are necessary to correlate the in vitro characteristics of a given fluorocarbon with its in vivo benefits.

An analysis of the therapeutic benefit or the usefulness of a given fluorocarbon or a lung additive containing fluorocarbon necessarily includes an analysis of a number of experimental parameters. These parameters include measurements of dynamic lung compliance, blood gas quantitations, alveolar/arterial oxygen tension ratios, lung water estimates, vascular protein leakage into the lung, inflammatory cell infiltrates, chest radiographs, ventilatory support indices over time and the like. Lung histologies from experimental subjects are used to demonstrate the resolution of atelectasis, evidence of necrosis, desquamation and inflammation. Individuals skilled in the art will be familiar with the test parameters listed above, therefore no further information needs be provided to facilitate these tests. Fluorocarbons providing beneficial test results in experimental animals are candidates for human use.

It is contemplated that there are a variety of uses for fluorocarbons in partial liquid breathing applications. Lung lavage can be used as both a diagnostic and therapeutic procedure. Diagnostic washings are often obtained by bronchoscopy. Diagnostic lavage requires the introduction of a small amount of fluid into the lungs in order to sample lung cells, exudate, or to obtain a sample for microbiological analysis.

Therefore, in accordance with one aspect of this invention, it is contemplated that PFOB or another fluorocarbon meeting the positive criteria disclosed herein could be used for such a procedure.

Large volume lung lavage is sometimes used as an emergency procedure to remove irritants, poisons or mucous plugs from the lungs. The procedure is also used in neonates to remove aspirated meconium. A pulmonary catheter is inserted into the bronchial airway and a solution is flushed into the lung. The use of saline in the lung for large volume lavage creates several problems. The procedure must be performed quickly because oxygen transfer at the membrane/air interface cannot occur efficiently in the presence of saline, and large volumes of saline flushed into the lungs effectively dilute and remove any functional lung surfactant present.

It is also contemplated that fluorocarbons could be used to inflate collapsed portions of lungs or collapsed lungs in general. The use of fluorocarbon to inflate portions of the lung is less damaging than the current methods employing increased air pressure. As noted previously, increased air pressures in lungs, particularly lungs that are compromised by disease or trauma, can produce barotrauma and induce additional lung damage.

If the lungs have been compromised by an irritant then surfactant replacement may be necessary. Oxygenatable fluorocarbons with positive spreading coefficients and low vapor pressures could provide an improved lavage fluid.

The fluorocarbon could also be provided as a liquid or aerosol in combination with an expectorant. The biocompatible fluorocarbon is easily taken into the lung and the expectorant additive facilitates the removal of the secretions of the bronchopulmonary mucous membrane. Examples of contemplated expectorants include but are not limited to ammonium carbonate, bromhexine hydrochloride and terpin hydrate.

In accordance with another aspect of this invention, it is further contemplated that PFOB or another suitable fluorocarbon could be used as a surfactant supplement. PFOB is able to spread easily over the surfaces of the lung and can facilitate oxygen transport. Any condition characterized by a lung surfactant deficiency would be amenable to this therapy. In addition to RDS in neonates, ARDS in adults caused by severe hypovolemic shock, lung contusion, diver's lung, post-traumatic respiratory distress, post-surgical atelectasis, septic shock, multiple organ failure, Mendelssohn's disease, obstructive lung disease, pneumonia, pulmonary edema or any other condition resulting in lung surfactant deficiency or respiratory distress are all candidates for fluorocarbon supplementation.

The amount of surfactant supplement given should be sufficient to cover the lung surface and should be at least 0.1% of the infant or adult's total lung capacity. In RDS, it is particularly important to stabilize the infant while minimizing and preventing additional lung damage for roughly four or five days. Those infants with RDS that survive this critical time frame have an 80% survival rate. The fluorocarbon is provided by direct instillation through an endotracheal tube. If the fluorocarbon is provided together with a surfactant powder, the powder can either be mixed into the fluorocarbon or provided to the infant or adult as an aerosol prior to fluorocarbon administration. The addition of lung surfactant powder to fluorocarbon provides a surfactant particulate dispersed throughout the fluorocarbon liquid.

During administration, the infant is placed in the right and left lateral decubitus positions while being mechanically or manually ventilated. Chest radiographs reveal that unlike other surfactant replacements in use that lack positive spreading coefficients, fluorocarbon is unilaterally distributed in the chest cavity. Since neonares are often difficult to intubate, only those individuals experienced in neonatal intubation should attempt this procedure. Mechanical ventilator usage and initial settings of breaths/minute, positive inspiratory pressures, positive-end expiratory pressure and inspiratory durations should be set initially as determined by the known standards for given infant weight and gestational ages, but should be monitored closely and altered accordingly as pulmonary function improves.

The use of partial liquid breathing is not restricted to cases where lung surfactant supplementation is necessary. Any condition requiring facilitated oxygen delivery, for example, is amenable to use of partial liquid breathing. Because the volume of fluorocarbon in the lung is such that liquid fluorocarbon is not exhaled by the patient, conventional ventilation equipment can be used. This overcomes a major obstacle to liquid breathing as contemplated in the prior art.

In addition to oxygen delivery, fluorocarbons can be used to remove endogenous or foreign material from the interior of the lungs. Lavage can be practiced using fluorocarbons as a substitute for conventional saline solutions. In this procedure, oxygen is provided to the patient by the fluorocarbon liquid itself, permitting a more lengthy and less dangerous lavage procedure. Moreover, removal of lung surfactant through the lavage is not a major problem because of the lung surfactant properties of selected fluorocarbons. The lavage procedure is further facilitated by the density of the fluorocarbon. The density of these liquids is generally 2, that is, twice that of water; they therefore tend to displace the material to be removed. This material can then be removed by removing the fluorocarbon, or can be removed from the surface of the fluorocarbon on which it will generally float.

In addition to the lung surfactant properties, the density of the fluorocarbon can facilitate inflation of collapsed alveoli and other portions of the lung. Under the influence of gravity, the fluorocarbon will apply positive pressure above and beyond breathing pressure to inflate such collapsed portions of the lung.

The use of fluorocarbons for partial liquid breathing requires a volume as little as 0.1% of the total lung capacity upon full natural inflation. However, it is preferred that the amount used be at least 0.2%, and more preferably at least 0.3% or 0.5% of the total lung capacity. Minimum amounts of 1%, 3%, or 5% of total lung capacity are preferred. It is additionally contemplated that fluorocarbon could be added in amounts up to about 50% of the total lung capacity.

Thus a method for partial liquid breathing is provided as another aspect of this invention.

Partial liquid breathing has a number of benefits over the total liquid breathing methods contemplated primarily for use in neonares. It appears that the difficult transition from total liquid breathing to total air breathing can be reduced by partial liquid breathing. The lungs are bathed in a biocompatible fluid. Lung trauma is minimized and this permits lung maturation and repair. Partial liquid breathing is more amenable to use in adults than total liquid breathing since air or gas can still be inhaled and exhaled. Partial liquid breathing can be used in conjunction with spontaneous, passive or mechanical ventilation. In addition, pharmacologic substances can be added to the fluorocarbon to further promote resolution of lung injury.

The amount of fluorocarbon introduced into the patient's lung is, at a minimum, necessarily sufficient to cover the surfaces of the lung. The actual volumes will depend on the treatment protocol, the weight and size of a patient as well as the lung capacity. It is contemplated that the useful range of fluorocarbon should be at least 0.1 ml of fluorocarbon liquid per kilogram patient body weight and not more than about 50 ml/kg.

It is further preferred that the maximum amount of fluorocarbon used for partial liquid breathing will approximate the volume of air remaining in a healthy lung of similar size following exhalation. The amount of air remaining in the lung at the end of exhalation can be measured in a number of ways that are known by those with skill in the art. Physiology-related equations relate the size, age, or weight of an individual to his exhaled lung volume.

Thus, during partial liquid breathing in accordance with the present invention, the lungs retain sufficient air capacity (above and beyond the volume of fluorocarbon in the lung) to permit inhalation such that normal breathing can proceed. The amount of air entering the lungs on inhalation is sufficient to oxygenate the fluorocarbon liquid. Further, the fluorocarbon liquid may be oxygenated prior to use to provide oxygen to the alveolar surfaces of the lung instantaneously upon initial contact with the fluorocarbon. If ventilation therapy is required, unlike total liquid breathing, standard ventilation equipment can be used. Partial liquid breathing can be used to reverse ventilary failure, as a prophylactic to prevent respiratory failure or as a therapeutic. As a therapeutic, fluorocarbon solution can be administered alone to minimize further lung trauma, or in combination with a given therapeutic agent. Fluorocarbon liquid can be provided together with a particulate therapeutic agent such as lung surfactant. These powder surfactants may be synthetic mixtures of phospholipids. For example, a mixture of diphosphatidylcholine and phosphoglycerol in a ratio of 7:3 could be mixed with a volume of fluorocarbon. Additionally, the surfactant powder may be in the form of dried extracts prepared from human or animal lung lavage. It was noted earlier that there are three major proteins (SP-A, SP-B and SP-C) associated with endogenous lung surfactant. Therefore, it is additionally contemplated that these proteins may be added as full length or as truncated fragments to the fluorocarbon mixture.

Partial liquid breathing according to the present invention is useful for a variety of medical applications. As a lavage, the technique is useful for meconium aspiration, gastric acid aspiration, asthma, cystic fibrosis, and pneumonia to remove adventitious agents. A fluorocarbon lavage may also be provided to patients with pulmonary alveolar proteinosis, bronchiectasis, atelectasis and immotile cilia syndrome. In addition, fluorocarbon may be used in emergency lavage procedures to remove food aspirates and other foreign materials.

Loss of lung resiliency can occur in both ARDS and RDS. The use of fluorocarbons in both of these syndromes is discussed above. In addition, lungs can become stiff from hydrocarbon aspiration, smoke inhalation, and lung contusions. Fluorocarbon therapy can be provided either as a surfactant supplement or for partial liquid breathing to supply oxygen to a patient or to facilitate a therapeutic regime. Treatment of pulmonary fibrosis, emphysema, and chronic bronchitis can all benefit from fluorocarbon therapy.

It has been noted above that a fluorocarbon liquid may be supplied to a patient in combination with a powdered surfactant or as a route for pulmonary drug delivery. Antibiotics and antivirals may be provided in combination with a fluorocarbon liquid. For example, cytomegalovirus can induce life-threatening cases of pneumonia in immunocompromised patients. These individuals often require ventilation therapy. Fluorocarbon administration in combination with the guanosine nucleoside analog, 9-(1,3-dihydroxy-2-propoxymethyl)guanine otherwise known as Ganciclovir or DHPG, may provide an effective therapy that could simultaneously inhibit viral replication and facilitate oxygen transport in the compromised lung.

In addition, anti-inflammatory agents could be added alone or in combination to the antimicrobial agents contemplated above. These anti-inflammatory agents include but are not limited to steroid and steroid derivatives or analgesics. The fluorocarbon could be administered together with a bronchodilator including but not limited to Albuterol, Isoetharines, perbuteral or an anti-allergenic agent.

The various pharmaceuticals that can be combined with fluorocarbons to provide therapy via administration to the lungs are too numerous to list. Except in some particularly preferred embodiments listed herein, the choice of pharmaceutical is not critical. Any non-damaging pharmaceutical that can be adsorbed across the lung membranes, or that can treat lung tissue, can be used. The amounts and frequency of administration for all the various possible pharmaceuticals have been established. It is not contemplated that these will be significantly different for administration through use of fluorocarbon vehicles in partial liquid breathing. Thus, those of ordinary skill in the art can determine the proper amount of pharmaceutical and the timing of the dosages in accordance with already-existing information and without undue experimentation.

The fluorocarbon liquid may also be administered in combination with an antimitotic agent for cancer therapy. Fluorocarbon liquid can also be used to facilitate oxygenation under anesthesia for patient's suffering from lung diseases such as emphysema, chronic bronchitis, and pulmonary fibrosis. Furthermore, fluorocarbons can be used for partial liquid breathing for any of the above mentioned maladies or any additional medical condition that would lend itself to this therapy.

The fluorocarbon liquid may advantageously be supplied to the physician in a sterile prepackaged form. Aliquots of the fluorocarbon are removed for administration under sterile conditions. Individual dosage volumes can be supplied for administration to newborns since newborn lung capacities are within a fairly narrow range. For those applications requiring a mixture of fluorocarbon and saline or powdered surfactant, each component can be provided separately and prepared for individual use. For lavage purposes, neat fluorocarbon or prepared emulsions of fluorocarbon and saline are provided prepackaged. It will be readily appreciated that there are a large number of potential additives that, in combination with fluorocarbon liquid, have important medical applications in the lung.

Those with skill in the art will readily appreciate the varied applications for fluorocarbon administration. Therefore the foregoing detailed description is to be clearly understood as given by way of illustration, the spirit and scope of this invention being limited solely by the appended claims.

What is claimed is:

1. A method of facilitating oxygen delivery through the lung of a patient comprising the steps of:

administering to the lung of the patient an effective oxygen delivery-facilitating amount of a fluorocarbon liquid having an equilibrium coefficient of spreading which is a positive number, said amount of administered fluorocarbon liquid not exceeding 35% of the functional residual capacity of the lung of the patient upon exhalation taking into account any positive or negative expiratory pressure applied to said patient's lung; and introducing a breathing gas into the lung wherein said introduced breathing gas physically admixes with and oxygenates said fluorocarbon liquid within the lung.

2. The method of claim 1 wherein said fluorocarbon liquid comprises a mixture of two or more fluorocarbons.

3. The method of claim 2 wherein the mixture of fluorocarbons comprises at least one fluorocarbon having an equilibrium coefficient of spreading which is a negative number.

4. The method of claim 1 wherein said fluorocarbon liquid further comprises a surfactant.

5. The method of claim 1 wherein said fluorocarbon liquid comprises a fluorocarbon-hydrocarbon compound.

6. The method of claim 1 wherein said fluorocarbon liquid comprises perfluorooctylbromide.

7. The method of claim 1 wherein said fluorocarbon liquid has a surface tension value less than 20 dynes/cm.

8. The method of claim 1 wherein said fluorocarbon liquid comprises a non-brominated fluorocarbon.

9. The method of claim 8 wherein said non-brominated fluorocarbon is perfluorooctylethane.

10. The method of claim 1 further comprising the step of introducing said breathing gas by spontaneous ventilation while the fluorocarbon liquid is in the lung.

11. The method of claim 1 further comprising the step of introducing said breathing gas using mechanical ventilation while the fluorocarbon liquid is in the lung.

12. The method of claim 1 wherein said fluorocarbon liquid is administered as an aerosol.

13. A method for the pulmonary administration of a pharmacologic agent to a patient comprising:
 administering to the lung of the patient an effective therapeutic amount of a pharmacologic agent dispersed in a volume of fluorocarbon liquid having an equilibrium coefficient of spreading which is a positive number, said administered volume of fluorocarbon liquid not exceeding 35% of the functional residual capacity of the lung of the patient upon exhalation taking into account any positive or negative expiratory pressure applied to said patient's lung; and
 introducing a breathing gas into the lung wherein said introduced breathing gas physically admixes with and oxygenates said fluorocarbon liquid within the lung.

14. The method of claim 13 wherein said fluorocarbon liquid comprises a mixture of two or more fluorocarbons.

15. The method of claim 14 wherein the mixture of fluorocarbons comprises at least one fluorocarbon having an equilibrium coefficient of spreading which is a negative number.

16. The method of claim 13 wherein said fluorocarbon liquid comprises perfluorooctylbromide.

17. The method of claim 13 wherein said fluorocarbon liquid comprises a fluorocarbon-hydrocarbon compound.

18. The method of claim 13 wherein said fluorocarbon liquid comprises a non-brominated fluorocarbon.

19. The method of claim 18 wherein said non-brominated fluorocarbon is perfluorooctylethane.

20. The method of claim 13 further comprising the step of introducing said breathing gas using spontaneous ventilation while the fluorocarbon liquid is in the lung.

21. The method of claim 13 further comprising the step of introducing said breathing gas using mechanical ventilation while the fluorocarbon liquid is in the lung.

22. The method of claim 13 wherein said pharmacologic agent is selected from the group consisting of bronchodilators, expectorants, lung surfactants, antibiotics, antivirals, anti-inflammatory agents, antimitotic agents, anesthetics and combinations thereof.

23. A method of facilitating oxygen delivery through the lung of a patient comprising the steps of:
 administering to the lung of the patient an effective oxygen delivery-facilitating amount of a non-brominated fluorocarbon liquid having an equilibrium coefficient of spreading which is a positive number, said amount of administered non-brominated fluorocarbon liquid not exceeding the functional residual capacity of the lung of the patient upon exhalation taking into account any positive or negative expiratory pressure applied to said patient's lung; and
 introducing a breathing gas into the lung wherein said introduced breathing gas physically admixes with and oxygenates said non-brominated fluorocarbon liquid within the lung.

24. The method of claim 23 wherein said non-brominated fluorocarbon liquid comprises a mixture of two or more non-brominated fluorocarbons.

25. The method of claim 24 wherein the mixture of non-brominated fluorocarbons comprises at least one non-brominated fluorocarbon having an equilibrium coefficient of spreading which is a negative number.

26. The method of claim 23 wherein said fluorocarbon liquid comprises a fluorocarbon-hydrocarbon compound.

27. The method of claim 23 wherein said non-brominated fluorocarbon liquid is a non-halogenated fluorocarbon liquid.

28. The method of claim 27 where said non-halogenated fluorocarbon liquid comprises perfluorooctylethane.

29. The method of claim 23 further comprising the step of introducing said breathing gas using spontaneous ventilation while the fluorocarbon liquid is in the lung.

30. The method of claim 23 further comprising the step of introducing said breathing gas using mechanical ventilation while the fluorocarbon liquid is in the lung.

31. A method for removing material from the lung of a patient comprising the steps of:
 administering to the lung of the patient an effective material displacing amount of a non-brominated fluorocarbon liquid having an equilibrium coefficient of spreading which is a positive number, said amount of administered non-brominated fluorocarbon liquid not exceeding the functional residual capacity of the lung of the patient upon exhalation taking into account any positive or negative expiratory pressure applied to said patient's lung wherein the administered non-brominated fluorocarbon liquid displaces material inside the lung;
 introducing a breathing gas while the non-brominated fluorocarbon liquid is in the lung; and
 removing said non-brominated fluorocarbon liquid together with at least a portion of the displaced material from the lung.

32. The method of claim 31 wherein said non-brominated fluorocarbon liquid comprises a mixture of two or more non-brominated fluorocarbons.

33. The method of claim 32 wherein the mixture of non-brominated fluorocarbons comprises at least one non-brominated fluorocarbon having an equilibrium coefficient of spreading which is a negative number.

34. The method of claim 31 wherein said fluorocarbon liquid comprises a fluorocarbon-hydrocarbon compound.

35. The method of claim 31 wherein said non-brominated fluorocarbon liquid is a non-halogenated fluorocarbon liquid.

36. The method of claim 35 where said non-halogenated fluorocarbon liquid comprises perfluorooctylethane.

37. The method of claim 31 further comprising the step of introducing said breathing gas using spontaneous ventilation.

38. The method of claim 31 further comprising the step of introducing said breathing gas using mechanical ventilation.

39. The method of claim 31 wherein the displaced material is selected from the group consisting of aspirated meconium, lung cells, exudate, irritants, poisons, mucous plugs, food aspirates and adventitious agents.

40. A method of facilitating oxygen delivery through the lung of a patient comprising the steps of:

administering to the lung of the patient an effective oxygen delivery-facilitating amount of a fluorocarbon liquid having an equilibrium coefficient of spreading which is a positive number and comprising fluorocarbons selected from the group consisting of bis(F-alkyl) ethanes, cyclic fluorocarbons, fluorinated amines, fluorocarbon esters, fluorocarbon thioesters, perfluoroalkylated ethers, perfluoroalkylated polyethers and fluorocarbon-hydrocarbon compounds, said amount of administered fluorocarbon liquid not exceeding the functional residual capacity of the lung of the patient upon exhalation taking into account any positive or negative expiatory pressure applied to said patient's lung; and introducing a breathing gas into the lung wherein said introduced breathing gas physically admixes with and oxygenates said non-brominated fluorocarbon liquid within the lung.

41. The method of claim 40 wherein said fluorocarbon liquid comprises a cyclic fluorocarbon selected from the group consisting of perfluorodecalin, F-adamantane, F-methyladamantane, F-1, 3-dimethyladamantane, F-dimethylbicyclo[3,3,1]nonane, F-dimethylbicyclo[3,3,1]nonane and combinations thereof.

42. The method of claim 40 wherein said fluorocarbon liquid comprises a perfluorinated amine selected from the group consisting of F-tripropylamine, F-tri-butylamine, F-4-methyloctahydroquinolizine, F-n-methyldecahydroisoquinoline, F-n-methyldecahydroquinoline, F-n-cyclohexylpurrolidine, F-2-butyltetrahydrofuran and combinations thereof.

43. The method of claim 40 further comprising the step of introducing said breathing gas using spontaneous ventilation while the non-brominated fluorocarbon liquid is in the lung.

44. The method of claim 40 further comprising the step of introducing said breathing gas using mechanical ventilation while the non-brominated fluorocarbon liquid is in the lung.

* * * * *

UNITED STATES PATENT AND TRADEMARK OFFICE
CERTIFICATE OF CORRECTION

PATENT NO.:     5,955,521

DATED:          September 21, 1999

INVENTOR(S):    Isaac B. Rufus and Hao A. Chen

It is certified that an error appears in the above-identified patent and that said Letters Patent is hereby corrected as shown below:

In Figure 1, top wave form, change "d" to --a--.

Signed and Sealed this

Fourteenth Day of March, 2000

Attest:

Q. TODD DICKINSON

Attesting Officer

Commissioner of Patents and Trademarks